(12) United States Patent
Tatake et al.

(10) Patent No.: US 7,109,385 B2
(45) Date of Patent: Sep. 19, 2006

(54) PROCESS FOR PRODUCING PHENOL

(75) Inventors: Prashant Anil Tatake, Mumbai (IN); Pramod Shankar Kumbhar, Mumbai (IN); Bharat Singh, Bangalore (IN); John William Fulmer, Mt. Vernon, IN (US); Sabyasachi Mandal, Bangalore (IN); Arun N. Kumar, Bangalore (IN); Rupesh Pawar, Maharashtra (IN)

(73) Assignee: General Electric Company, Schenectady, NY (US)

( * ) Notice: Subject to any disclaimer, the term of this patent is extended or adjusted under 35 U.S.C. 154(b) by 31 days.

(21) Appl. No.: 11/092,078

(22) Filed: Mar. 29, 2005

(65) Prior Publication Data

US 2005/0222466 A1    Oct. 6, 2005

Related U.S. Application Data

(63) Continuation-in-part of application No. 10/815,575, filed on Mar. 31, 2004, now abandoned.

(51) Int. Cl.
 *C07C 37/08* (2006.01)
(52) U.S. Cl. ..................... 568/798; 568/728
(58) Field of Classification Search ............... 568/798, 568/728
 See application file for complete search history.

(56) References Cited

U.S. PATENT DOCUMENTS

| | | | |
|---|---|---|---|
| 2,626,281 A | 1/1953 | Joris | |
| 2,628,983 A | 2/1953 | Aller et al. | |
| 2,663,735 A | 12/1953 | Filar et al. | |
| 2,715,145 A | 8/1955 | Bewley et al. | |
| 2,757,209 A | 7/1956 | Joris | |
| 2,904,592 A | 9/1959 | Ellis et al. | |
| 2,986,583 A | 5/1961 | Robbers et al. | |
| 3,029,294 A | 4/1962 | Keeble | |
| 3,271,457 A | 9/1966 | Bewley et al. | |
| 3,335,070 A | 8/1967 | Adams | |
| 3,454,653 A | 7/1969 | Larson | |
| 3,692,845 A | 9/1972 | Cheema et al. | |
| 4,016,213 A | 4/1977 | Yeh et al. | |
| 4,209,465 A | 6/1980 | Austin et al. | |
| 4,246,203 A | 1/1981 | Wirth | |
| 4,310,712 A | 1/1982 | Langley | |
| 4,358,618 A | 11/1982 | Sifniades et al. | |
| 5,245,090 A | 9/1993 | DeCaria et al. | |
| 5,254,751 A | 10/1993 | Zakoshansky | |
| 5,371,305 A | 12/1994 | Hood | |
| 5,414,151 A | 5/1995 | Pressman et al. | |
| 5,414,154 A | 5/1995 | Jenczewski et al. | |
| 5,430,200 A | 7/1995 | Hood | |
| 5,463,136 A | 10/1995 | Blackbourn et al. | |
| 5,502,259 A | 3/1996 | Zakoshansky et al. | |
| 5,530,166 A | 6/1996 | Zakoshansky et al. | |
| 5,648,561 A | 7/1997 | Tan et al. | |
| 5,998,677 A | 12/1999 | Yasaka et al. | |
| 6,057,483 A | 5/2000 | Zakoshansky et al. | |
| 6,066,767 A | 5/2000 | Zakoshansky et al. | |
| 6,201,157 B1 | 3/2001 | Keenan | |
| 6,225,513 B1 | 5/2001 | Zakoshansky et al. | |
| 6,303,825 B1 | 10/2001 | Gerlich et al. | |
| 6,307,112 B1 | 10/2001 | Weber et al. | |
| 6,388,144 B1 | 5/2002 | Wijesekera et al. | |
| 6,489,159 B1 | 12/2002 | Chenchik et al. | |
| 6,630,608 B1 | 10/2003 | Tanger et al. | |
| 2002/0040165 A1 | 4/2002 | Hertzog et al. | |
| 2002/0058845 A1 | 5/2002 | Levin et al. | |
| 2002/0068840 A1 | 6/2002 | Weber et al. | |
| 2003/0220528 A1 | 11/2003 | Weber et al. | |

FOREIGN PATENT DOCUMENTS

| | | |
|---|---|---|
| EP | 0589588 A1 | 3/1994 |
| GB | 629429 | 8/1947 |
| GB | 864486 | 5/1958 |
| GB | 865677 | 5/1959 |
| GB | 920864 | 7/1961 |
| GB | GB 1 108 584 | 7/1965 |
| GB | GB 1 202 687 | 3/1969 |
| GB | 1381398 | 3/1972 |

*Primary Examiner*—Michael L. Shippen

(57) ABSTRACT

A process for producing a phenol product generally comprises a first step comprising reacting in a first reactor a feed stream comprising cumene hydroperoxide and water with an acid catalyst to produce an effluent comprising the phenol product, acetone, and at least 1% by weight residual cumene hydroperoxide, and a second step comprising passing the effluent into a second reactor and decomposing the residual cumene hydroperoxide, wherein during said process the ratio of phenol to acetone is maintained at a molar ratio of greater than 1:1, and wherein the water in each of the first and second steps is present in an amount more than 0 and less than or equal to 5 weight percent based on the total weight of the feed stream or effluent, and wherein the process is continuous.

23 Claims, 1 Drawing Sheet

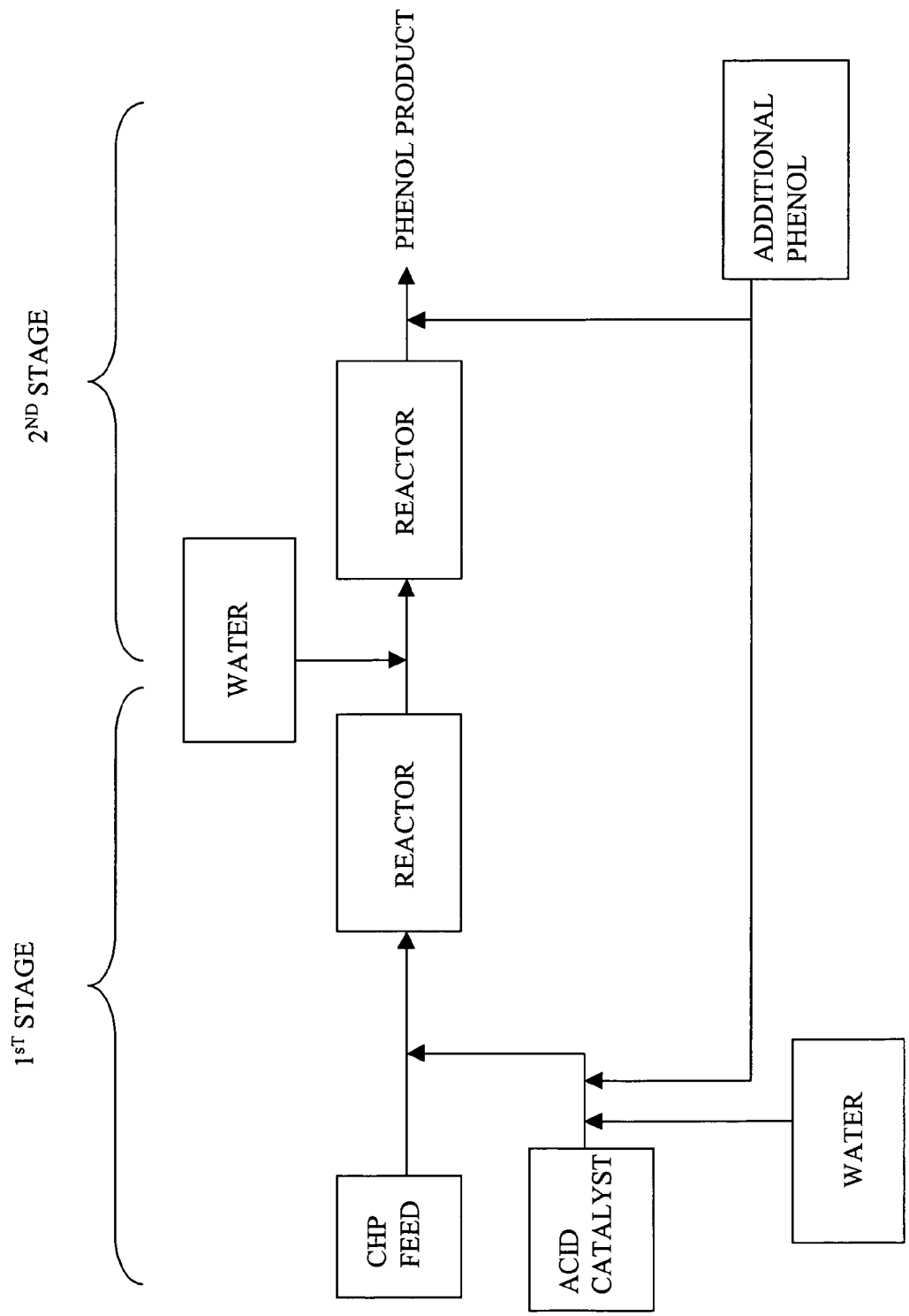

PROCESS FOR PRODUCING PHENOL

CROSS REFERENCE TO RELATED APPLICATIONS

The present application is a continuation-in-part application of and claims priority to, U.S. patent application Ser. No. 10/815,575 filed on Mar. 31, 2004, now abandoned, incorporated herein by reference in its entirety

BACKGROUND

The present disclosure generally relates to a method for producing a phenol stream with reduced by-products. More particularly the present invention relates to a two-step continuous method for producing a phenol stream with reduced by-products.

The cleavage reaction of cumene hydroperoxide (CHP) in the manufacture of phenol and acetone from cumene is well known. Today most modern CHP cleavage processes are carried out in a continuous flow manner and utilize the so-called "2-stage cleavage process", which provides the best economics because, in addition to making phenol and acetone from CHP, it recovers cumene value from the by-product DMBA formed in the prior cumene oxidation step. Such prior art 2-stage cleavage processes are described in U.S. Pat. Nos. 6,307,112, 6,225,513, 6,201,157, 6,057,483, 5,998,677, 5,530,166, 54,63,136, 5,430,200, 5,371,305, 5,254,751, and 4,358,618.

In the $1^{st}$ cleavage stage, a technical grade CHP feed is predominantly decomposed with an acid to form phenol and acetone in equal molar amounts, however, at the same time the reaction conditions of the $1^{st}$ stage are carefully controlled to allow a small amount of CHP to remain undecomposed so that it can react with the DMBA in the incoming feed stream to produce dicumylperoxide (DCP). This $1^{st}$ stage process can utilize a constant boiling or acetone-refluxing type reactor design for the CHP cleavage reaction, or it can utilize a multiplicity of non-boiling CHP decomposers.

In the $2^{nd}$ stage of the cleavage process, the DCP that was generated in the $1^{st}$ stage is decomposed under controlled conditions to form acetone, phenol, and alpha-methylstryrene (AMS) in high yield with little tar formation. The AMS formed here from the DCP can later be easily converted to cumene via hydrogenation, and recycled for reuse. Thus, the overall effect is that the DMBA by-product is recovered as valuable cumene and prevented from converting to tarry by-product wastes.

To encourage the formation of DCP in the $1^{st}$ stage, prior art processes generally use excess acetone to retard the acidic decomposition of CHP and allow it to accumulate in small part. The amounts of additional acetone described in the prior art as effective are about 10–40% excess over the amount of "in-situ" acetone generated during the CHP decomposition reaction. Thus, the acetone:phenol molar ratio is typically maintained at 1.1:1 to 1.5:1 during the cleavage reaction medium.

Although extra acetone addition can be an effective method for inhibiting the CHP decomposition reaction and enhancing DCP formation, such a cleavage process operating with a high acetone:phenol ratio is subject to the disadvantage of forming increased levels of other harmful "carbonyl-type" by-products such as hydroxyacetone (also known as HA or acetol) and mesityl oxide (MO).

Moreover, as a result of the carbonyl impurities formed during cleavage, the resulting phenol and acetone products have to be separated from these undesirable by-products and impurities using energy intensive processes. For example, the presence of acetol impurities in the phenol product renders quality unacceptable for many end-use applications, such as in the production of bisphenol-A, diphenyl carbonate, and polycarbonate. Furthermore, the phenol product that contains acetol impurities tends to discolor upon aging, or during subsequent reactions, such as during sulfonation and chlorination reactions.

The hydroxyacetone impurity has proven to be particularly difficult to remove from the phenol product in a downstream process since it co-distills at a similar temperature as phenol during thermal separation processes, e.g., rectification processes. Because of this, current thermal separation processes are generally ineffective at purifying the phenol product to remove the acetol impurity. As a result various chemical removal methods are commonly used in the downstream phenol process for carbonyls removal. This includes treatment with various acids, bases, ion exchange resins, zeolites, etc. All of these approaches are costly, requiring expensive reagents and additional equipment.

To date little or no progress has been made in reducing the acetol by-product amount in the phenol process at its point of generation, that is the CHP cleavage step. Reducing the amount of hydroxyacetone and other carbonyls early in the process at the CHP cleavage process would greatly simplify the downstream purification steps, reducing investment and energy consumption.

Accordingly, there is a need in the art for an improved continuous process for producing phenol from CHP that does not produce the harmful "carbonyl-type" by-products that is obtained from the use of excess acetone during the cleavage reaction. Such a process would desirably be a more economically favorable method for producing the purified phenol product.

BRIEF SUMMARY

In one embodiment, a process for producing a phenol product comprises a first step comprising reacting in a first reactor a feed stream comprising cumene hydroperoxide and water with an acid catalyst to produce an effluent comprising the phenol product, acetone, and at least 1% by weight residual cumene hydroperoxide, and a second step comprising passing the effluent into a second reactor and decomposing the residual cumene hydroperoxide, wherein during said process the ratio of phenol to acetone is maintained at a molar ratio of greater than 1:1, and wherein the water in each of the first and second steps is present in an amount more than 0 and less than or equal to 5 weight percent based on the total weight of the feed stream or effluent, and wherein the process is continuous.

In another embodiment, a process for producing a phenol product comprises a first step comprising reacting in a first reactor a feed stream comprising cumene hydroperoxide and water with an acid catalyst to produce an effluent comprising the phenol product, acetone, and dicumyl peroxide; and a second step comprising passing the effluent into a second reactor and decomposing the dicumyl peroxide, wherein during said process a ratio of phenol to acetone is maintained at a molar ratio of greater than 1:1, wherein the phenol product comprises less than or equal to 40 parts per million hydroxyacetone, and wherein the process is continuous The present disclosure may be understood more readily by reference to the following detailed description of the various features of the disclosure and the examples included therein.

BRIEF DESCRIPTION OF THE DRAWINGS

The FIGURE illustrates a process flow for producing a phenol product in accordance with one embodiment.

DETAILED DESCRIPTION

The disclosure may be understood more readily by reference to the following detailed description of preferred embodiments and the examples included therein. In the following specification and the claims which follow, reference will be made to a number of terms that shall be defined to have the following meanings: the singular forms "a", "an" and "the" include plural referents unless the context clearly dictates otherwise. "Optional" or "optionally" means that the subsequently described event or circumstance may or may not occur, and that the description includes instances where the event occurs and instances where it does not. The modifier "about" used in connection with a quantity is inclusive of the stated value and has the meaning dictated by the context (e.g., includes the degree of error associated with measurement of the particular quantity).

By implementing the process outlined in the present disclosure it is possible to improve the purity of the phenol product by advantageously suppressing the formation of hydroxyacetone during an acid catalyzed cleavage process of cumene hydroperoxide The process as shown in the FIGURE generally comprises a continuous for the manufacture of the phenol product. In one embodiment, a first step generally comprises reacting in a first reactor a feed stream comprising cumene hydroperoxide and water with an acid catalyst to produce an effluent comprising the phenol product, acetone, and at least 1% by weight residual cumene hydroperoxide. Without being bound to theory it is believed that, reacting the cumene hydroperoxide with the acid catalyst in the presence of water, serves to inhibit the cleavage of CHP such that the effluent from the first step contains at least 1% by weight residual CHP. In one another embodiment the first step comprises reacting in a first reactor a feed stream comprising cumene hydroperoxide and water with an acid catalyst to produce an effluent comprising the phenol product, acetone, and dicumyl peroxide.

In one embodiment the second step comprises passing the effluent into a second reactor and; decomposing the residual cumene hydroperoxide in the effluent obtained from the first step. In yet another embodiment the second step comprises passing the effluent into a second reactor and decomposing the dicumyl peroxide; in the effluent obtained from the first step. In various other embodiments in both the first and the second steps the ratio of phenol to acetone is maintained at a molar ratio of greater than 1:1 during the process and water in each of the first and second steps is present in an amount more than 0 and less than or equal to 5 weight percent based on the total weight of the feed stream or effluent. In one embodiment in both the first and the second steps the ratio of phenol to acetone is maintained at a molar ratio of greater than 1.2:1 during the process. In yet another embodiment in both the first and the second steps the ratio of phenol to acetone is maintained at a molar ratio of greater than 1.5:1 during the process. In one embodiment, the amount of water is maintained greater than or equal to 0.8 wt % to 4 wt %, and in other embodiments, the amount of water is maintained greater than or equal to 0.8 wt % to 2 wt %. The process advantageously produces the phenol product with less than or equal to 40 parts per million of hydroxyacetone.

The decomposition reaction of CHP in the first step is substantially instantaneous, and as such, the residence time of the feed stream in the first step is typically low so as to provide at least 1% residual CHP in the resulting effluent. In one embodiment, the residence time of the feed stream in the first step is from about 30 seconds to about 4 minutes, and more specifically, the residence time taken for the CHP decomposition is about 35 seconds to 3 minutes. In yet another embodiment, the residence time of the feed stream in the first step is about 1 minute to about 2 minutes. In order to obtain the desired residence time noted above in the first step, the weighted hourly space velocity (hereinafter referred to as WUSV) of the feed stream in the first step varies from about 40 to about 80 and more specifically from 50 to 70. In one embodiment, the WHSV varies from about 55 to 60.

In various embodiments, the decomposition of CHP in the first step is carried out at a temperature effective to promote decomposition and produce the phenol product, results in minimum formation of byproducts, and maintains at least about 1% residual CHP in the resultant phenol product. As used herein, the term residual CHP refers to unreacted and undecomposed CHP. In one embodiment, the temperature in the first step is from about 45° C. to about 75° C., and more specifically the temperature is about 50° C. to about 65° C. In another embodiment, the temperature in the first step is maintained at about 55° C. to about 60° C.

Any suitable acid-catalyst may be used in first and second steps. Suitable acid catalysts include, but are not limited to, mineral acids, organic acids, acidic clays, and acidic ion exchange resins. Exemplary acid catalysts include, but are not intended to be limited to, sulphuric acid, phosphoric acid, p-toluene sulphonic acid, benzene sulphonic acid, trichloroacetic acid, acid-treated bentonite, a naturally occurring acidic clay and sulphonated styrene-divinyl benzene resin. In one embodiment, the acid-catalyst employed is sulphuric acid. Other suitable acid catalysts will be apparent to those skilled in the art in view of this disclosure.

The quantity of acid catalyst employed in the first step is an amount effective to promote decomposition of the CHP. In one embodiment, the amount of catalyst employed in the first step is about 25 parts per million (ppm) to about 750 ppm based on the total weight of the feed stream and, more specifically the amount of catalyst is about 100 ppm to about 650 ppm. In another embodiment, the amount of catalyst employed in the first step is about 150 ppm to about 300 ppm based on the total weight of the feed stream.

During the first step, CHP decomposes to produce in the effluent phenol, acetone, hydroxyacetone, and dicumyl peroxide (DCP), among others. The acid catalyst contained in the effluent is then subsequently neutralized, i.e., increasing the pH of the effluent to greater than about 7 before passing the effluent through the second step. In one embodiment, the neutralization is effected by using an aqueous ammonia solution. In another embodiment, neutralization is carried out by adding about 0.5 weight percent to about 4 weight percent of the aqueous ammonia solution to the effluent. This reduces the amount of acid catalyst in the effluent to about 0 ppm to about 600 ppm, and more specifically to about 25 ppm to about 400 ppm. In one embodiment, the amount of acid catalyst remaining in the effluent after neutralization ranges from about 50 ppm to about 200 ppm.

Without being bound to theory it is believed that DCP is formed in the first step by the reaction of any dimethyl benzylalcohol (DMBA) present in the feed stream with the CHP. The DCP so formed in the first step is subsequently decomposed in the second step in the presence of water and the acid catalyst to produce additional amounts of the phenol product. The reaction of DMBA is advantageous, since if left unreacted, the presence of DMBA in the phenol product would lead to tar formation in subsequent processing. Hence, it is advantageous to reduce the DMBA content as low as possible by reaction with CHP to form DCP.

In one embodiment the process is carried out in a continuous manner. In one other embodiment the process is carried out in a continuous two-step manner. In one embodiment the first reactor is a continuously stirred glass lined reactor. In one embodiment the second reactor is a continuously stirred tank reactor fitted with baffles for improved mixing, which results in increased decomposition of DCP to phenol and acetone. In one embodiment the baffles are crisscross baffles that cross one another in opposite directions helping to create maximum turbulence. In addition to providing improved mixing, baffles are also believed to help prevent back flow of liquid and thereby improve DCP decomposition.

In various embodiment, the temperature maintained in the second step is about 100° C. to about 160° C., and specifically, at about 110° C. to 150° C. In one embodiment, the temperature is about 120° C. to 140° C.

In various embodiments, the pressure maintained during the second step is about 50 pounds per square inch of gauge (psig) to about 150 psig, and specifically, at about 70 to about 130 psig. In one embodiment, the pressure is about 80 psig to about 105 psig.

In one embodiment the residence time in the second step is about 5 minutes to about 60 minutes. In another embodiment, the residence time is about 10 minutes to about 45 minutes. In yet another embodiment, the residence time of the effluent in second step is about 12 minutes to about 25 minutes. In order to obtain the desired residence times, the WHSV varies from about 8 to about 20, and more specifically, from 10 to 15. In one embodiment, the WHSV varies from about 10 to 12.

The phenol product is then fed to a thermal separation unit, wherein the purified phenol product can be separated and recovered. Thermal separation can be accomplished by distillation or through rectification.

In another embodiment, a process for enhancing the decomposition of CHP to phenol and acetone in the first step comprises maintaining the total amount of water in the process such that the amount of water in each step is greater than 0 weight percent and does not exceed 5 weight percent based on the weight of the feed stream or effluent. Without being bound to theory it is believed that in the first step CHP in addition to getting decomposed to phenol and acetone also reacts with DMBA present initially in the feed stream to form DCP in the presence of water in the feed stream under the conditions prevailing in the first step. The DCP so-formed contributes to the formation of additional phenol by getting decomposed under the conditions prevailing in the second step in the presence of water. In one embodiment, the amount of water required in each step ranges from 0.8 to 4 weight percent. In another embodiment the amount of water ranges from 0.8 to 2 weight percent. The process described hereinabove enables the production of phenol product with reduced hydroxyacetone content at relatively low operating temperatures and with higher yields.

Advantageously, this technique provides the ability to produce the phenol product and acetone at relatively high purity and with lower color, as well as the ability to operate the overall phenol production plant at a higher production rate, which represents a significant commercial advantage. Without being bound by theory, the higher production rate is a consequence of the lower levels of hydroxyacetone present in the effluent and phenol product produced as described above. Also, it has been surprisingly observed that maintaining a residual CHP of at least about 1% in the effluent flowing into the second step increases the overall yield of the phenol product. The residual CHP reacts with DMBA to produce DCP, which in turn decomposes to increase the overall yield of the phenol product. A lower hydroxyacetone level (i.e., an hydroxyacetone concentration less than 40 ppm) in the phenol product allows for a higher throughput in the downstream distillation operation, thereby leading to a lower cost process for producing purer phenol.

The phenol product obtained by the process may be used in the preparation of diphenylcarbonate or bisphenols. Diphenylcarbonate can be made by a variety of procedures including the phosgenation of phenol in an aqueous environment (slurry or melt) or in a solvent such as methylene chloride or by transesterification of dimethylcarbonate with phenol. A more direct procedure for making diphenylcarbonate involves the carbonylation of phenol with carbon monoxide. A transition metal catalyst such as a palladium catalyst is used in the carbonylation route often in combination with a quaternary ammonium halide as is generally known by those skilled in the art. Another procedure for making diphenylcarbonate involves the reaction between a cycloalkylene carbonate and phenol. Bisphenols may be synthesized by a condensation reaction between phenol and a carbonyl-containing compound in the presence of an acid catalyst. Numerous types of acid catalysts have been used in this type of condensation reaction including hydrochloric acid, perchloric acid, borontrifluoride as well as solid acid catalysts including zeolites, acid clays, heteropolyacids and ion-exchange resins.

The bisphenols and diphenyl carbonates can be used to prepare bisphenol polycarbonates by methods known in the art. Suitable methods of preparing the polycarbonates include, but are not intended to be limited to, an interfacial method, wherein bisphenol and phosgene or bisphenol and diphenyl carbonate are directly reacted in a molten state to undergo ester interchange reaction; an ester interchange that is usually effected at temperatures of 250° C. or 330° C. in presence of catalysts such as organic acid salts, inorganic acid salts, oxides, hydroxides or hydrides of metals or alcoholates; and a phase boundary process under catalysis by tertiary amines, tertiary amines may also be used for the preparation of polycarbonate through the reaction of bisphenol and phosgene. Alternately, a polycarbonate can be prepared by the reaction of diphenyl carbonate and bisphenol in presence of an alkaline catalyst at high temperatures by using a melt transesterification polymerization method.

The disclosure is further illustrated by the following non-limiting examples.

EXAMPLES

In these Examples, the analysis of hydroxyacetone was carried out on an Agilent 6890 Gas chromatograph (GC). GC separation was carried out on glass column with a length 24 inches & ¼ inch outer diameter, configured for on column injection, packed with chromsorb 102 80/100 mesh, with helium as carrier gas at 30 milliliters per minute (ml/min). The injector temperature was maintained at 160° C. and the detector temperature was maintained at 250° C. The initial column temperature was kept at 110° C. for 3 minutes hold time, this was followed by a temperature increase at 7° C. per minute to reach 150° C., held for 2 minutes, at 150° C., followed by a temperature increase at 10° C. per minute to reach 200° C. and held at 200° C. for 15 minutes. The column was calibrated with standard hydroxyacetone (obtained from Aldrich Chemical Company, 97% pure) at a concentration ranging from 5 parts per million (ppm) to 244 ppm made in a 50:50 mixture of cumene and phenol. Hydroxyacetone in the reaction mixture was analyzed by neutralizing a test sample with anhydrous sodium carbonate (around 1.5 g of sodium carbonate is utilized to neutralize 10 g of sample reaction mixture). The sample reaction mixture was directly injected into the GC without dilution to obtain maximum intensity of the HA peak in the sample.

The analysis of cumene, AMS, acetophenone, DMBA, and DCP was carried out on an Agilent 6890 column Gas chromatograph. GC separation was carried out on SBP-1 liquid phase, 30 meter length, 0.53 millimeter inner diameter and a film thickness of 3.0 micrometer. The GC was initially calibrated using standard Aldrich samples of cumene, AMS, acetophenone, DMBA, and DCP diluted in 50:50 acetone and phenol mixture. The diluted standard samples were injected into GC with an on-column injector. About 10 grams of sample reaction mixture was neutralized with anhydrous sodium carbonate (1.5 grams) to avoid degradation and further reaction of cleavage products. The stabilized reaction mixture was then weighed accurately and diluted with an equal weight of acetone. The solution was than injected into an on-column GC. Samples at specific time intervals were analyzed and compared to the GC chromatogram of a standard to determine the cleavage of CHP to corresponding products.

The analysis of phenol was carried out on a Shimadzu GC. The GC separation was carried out on HP-50 column, 30 meter length, 0.25 millimeter inner diameter and 0.25 micrometer film thickness. The injector and detector temperature were kept at 290° C., split ratio of 1:100 was used to avoid saturation of column. The initial column temperature was kept at 50° C., which was followed by a temperature increase of 8° C. per minute to 240° C. and then held at 240° C. for 10 minutes. The GC was initially calibrated with phenol obtained from Aldrich. The phenol standard was prepared by diluting phenol in acetonitrile to obtain various concentration levels of phenol. The diluted standard samples were then injected into the GC. Samples were analyzed by weighing about 100 milligrams of reaction mixture and diluting the reaction mixture with acetonitrile to a homogeneous mixture of 10 milliliters, and injecting into a GC with HP-50 Column. Samples at specific time intervals during reaction were analyzed and compared to the GC chromatogram of the standard sample to determine percentage of phenol formed by cleavage of CHP.

Comparative Examples 1, 2, and 3

In these comparative examples, CHP was decomposed in a prior art two-step continuous process to obtain a phenol product, wherein the molar ratio of the phenol to acetone was maintained at 0.77:1 as in Comparative Example 1 or 1:1 as in Comparative Examples 2 and 3. The process generally included adding CHP to an agitated mixture of phenol, acetone, and sulfuric acid. The composition of the feed stream entering the reactor is illustrated in Table 1.

In the first step of the continuous process, a typical synthetic feed stream comprising phenol, acetone, and CHP was fed to a glass reactor fitted with a condenser having a capacity of about 150 milliliters through the respective inlets for the feed stream and acid catalyst. The reactor was also fitted with a temperature probe to monitor the temperature and external heating/cooling jacket to maintain the temperature. The contents of the reactor were continuously stirred with a magnetic stirrer. The composition of the feed stream and amount of catalyst added is illustrated in Table I below. The reactor in the first step was maintained at 50° C. The residence time of the feed stream was monitored and maintained at 1 minute in the first step of the process. Sulfuric acid (98%) was added separately and simultaneously with the feed stream to the reactor. The resultant effluent was analyzed for residual CHP, DMBA, hydroxyacetone, DCP and phenol. Results of the analysis are included in Table 2 below. The resulting effluent was then neutralized using 1% aqueous ammonia solution, to result in a mixture containing 100 ppm acid catalyst, in a neutralizer. This neutralized effluent was then fed to the second step reactor. The reactor used in the second step was a stainless steel chamber having a capacity of 300 ml and is fitted with criss-cross baffles to ensure efficient mixing of the reactor contents. The second step reactor is maintained at 130° C. and under a pressure of 90 psig. The residence time maintained in the second step was 17 minutes. The resulting mixture from second step was analyzed using gas chromatographic techniques. The results of the analysis are included in Table 2 below.

TABLE I

| Examples | Comparative Example 1 | Comparative Example 2 | Comparative Example 3 |
|---|---|---|---|
| Phenol/Acetone Molar ratio | 0.77 | 1.00 | 1.00 |
| | Composition of feed stream | | |
| Phenol (wt. %) | 41.59 | 46.18 | 45.16 |
| Acetone (wt. %) | 33.10 | 28.50 | 27.94 |
| Cumene (wt. %) | 11.74 | 11.71 | 11.84 |
| Water (wt. %) | 0.76 | 0.78 | 2.04 |
| CHP (wt. %) | 6.13 | 6.15 | 5.99 |
| DMBA (wt. %) | 0.67 | 0.66 | 1.14 |
| DCP (wt. %) | 4.89 | 4.89 | 4.75 |
| AMS (wt. %) | 0.42 | 0.42 | 0.42 |
| Acetophenone (wt. %) | 0.61 | 0.61 | 0.59 |
| Sulfuric Acid (ppm) | 208 | 206 | 205 |

TABLE 2

| | First Step | | | | | Second Step | | | |
|---|---|---|---|---|---|---|---|---|---|
| Comp. Examples | Phenol Yield (wt. %) | DCP (wt. %) | HA (ppm) | CHP (wt. %) | DMBA (wt. %) | Phenol Yield (wt. %) | HA (ppm) | DMBA (wt. %) | AMS (wt. %) |
| 1 | 45.73 | 4.26 | 41.07 | 0.90 | 0.03 | 47.50 | 91.80 | 0.03 | 2.32 |
| 2 | 52.60 | 4.25 | 27.40 | 0.74 | 0.60 | 47.62 | 37.40 | 0.37 | 0.95 |
| 3 | 49.1 | 4.22 | 14.9 | 0.348 | 1.114 | 45.61 | 12.6 | 0.759 | 0.58 |

Examples 1–3

In these examples, CHP was decomposed in a continuous 2-STEP process to obtain a phenol product, wherein the molar ratio of phenol to acetone was greater than or equal to 1.2:1, and the effluent produced from the first step contained at least 1% residual CHP. Table 3 illustrates the composition of the feed stream. The process generally included adding CHP to an agitated mixture of phenol, acetone, and sulfuric acid.

In the first step of the continuous process, a typical synthetic feed composition having phenol, acetone, and CHP was fed to a glass reactor fitted with a condenser having a capacity of about 150 milliliters through the respective inlets for the feed stream and acid catalyst. The reactor was also fitted with a temperature probe to monitor the temperature and external heating/cooling jacket to maintain the temperature. The contents of the reactor were continuously stirred with a magnetic stirrer. The composition of the feed stream and amount of catalyst added is illustrated in Table II below. The reactor in the first step was maintained at 50° C. The residence time of the feed stream was monitored and maintained at 1 minute in the first step of the process. Sulfuric acid (98%) of concentration was added separately and simultaneously with the feed stream to the reactor. The resultant effluent was analyzed for residual CHP, DMBA, hydroxyacetone, DCP and phenol. Results of the analysis are included in Table 4 below. The resulting mixture was the neutralized using 1% aqueous ammonia solution to result in a mixture containing 100 ppm acid catalyst, in a neutralizer. This neutralized effluent was then fed to the second step reactor. The reactor used in the second step was a stainless steel chamber having a capacity of 300 ml and is fitted with criss-cross baffles to ensure efficient mixing of the reactor contents. The second step reactor is maintained at 130° C. and under a pressure of 90 psig. The residence time maintained in the second step was 17 minutes. The resulting mixture from second step was analyzed using gas chromatographic techniques. The results of the analysis are included in Table 4 below.

TABLE 3

|  | Example 1 | Example 2 | Example 3 |
|---|---|---|---|
| Phenol/Acetone Molar ratio | 1.20 | 2.00 | 1.20 |
|  | Composition of feed stream | | |
| Phenol (wt. %) | 49.38 | 57.07 | 48.2 |
| Acetone (wt. %) | 25.39 | 17.61 | 24.86 |
| Cumene (wt. %) | 11.60 | 11.73 | 11.83 |
| Water (wt. %) | 0.79 | 0.78 | 1.990 |
| CHP (wt. %) | 6.14 | 6.11 | 6.08 |
| DMBA (wt. %) | 0.66 | 0.66 | 1.13 |
| DCP (wt. %) | 4.90 | 4.89 | 4.76 |
| AMS (wt. %) | 0.42 | 0.42 | 0.419 |
| Acetophenone (wt. %) | 0.61 | 0.61 | 0.604 |
| Sulfuric acid (ppm) | 201 | 205 | 205 |

While the disclosure has been described with reference to exemplary embodiments, it will be understood by those skilled in the art that various changes may be made and equivalents may be substituted for elements thereof without departing from the scope and spirit of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A process for producing a phenol product, the process comprising;
   a first step comprising reacting in a first reactor a feed stream comprising cumene hydroperoxide and water with an acid catalyst to produce an effluent comprising the phenol product, acetone, and at least 1% by weight residual cumene hydroperoxide; and
   a second step comprising passing the effluent into a second reactor and decomposing the residual cumene hydroperoxide, wherein during said process a ratio of phenol to acetone is maintained at a molar ratio of greater than 1:1, and wherein the water in each of the first and second steps is present in an amount more than 0 and less than or equal to 5 weight percent based on the total weight of the feed stream or effluent, and wherein the process is continuous.

2. The process of claim 1, wherein the ratio of phenol to acetone is maintained at a molar ratio of greater than 1.2:1.

3. The process of claim 1, wherein the phenol product contains less than or equal to 40 parts per million of hydroxyacetone based on a total weight of the phenol product.

4. The process of claim 1 wherein the first step is maintained at a temperature of 45° C. to 75° C.

5. The process of claim 1, wherein the feed stream in the first step has a residence time of 30 seconds to 4 minutes.

6. The process of claim 1, wherein the feed stream in the first step is passed at a weighted hourly space velocity of 40 to 80.

7. The process of claim 1, wherein the second step is maintained at a temperature of 100° C. to 160° C.

8. The process of claim 1, wherein the effluent has a residence time of 5 minutes to 60 minutes in the second step.

9. The process of claim 1, wherein the effluent is passed at a weighted hourly space velocity of 8 to 20 in the second step.

10. The process of claim 1, wherein the acid-catalyst is selected from the group consisting of mineral acids, organic acids, acidic clays, and acidic ion exchange resins.

TABLE 4

|  | First Step | | | | | Second Step | | | |
|---|---|---|---|---|---|---|---|---|---|
|  | Phenol Yield (wt. %) | DCP (wt. %) | HA (ppm) | CHP (wt. %) | DMBA (wt. %) | Phenol Yield (wt. %) | HA (ppm) | DMBA (wt. %) | AMS (wt. %) |
| 1 | 53.20 | 4.34 | 15.12 | 1.32 | 0.42 | 48.80 | 31.34 | 0.33 | 0.84 |
| 2 | 61.50 | 4.15 | 5.65 | 1.70 | 0.33 | 59.08 | 20.87 | 0.26 | 1.06 |
| 3 | 50.8 | 4.28 | 13.2 | 1.00 | 1.422 | 48.16 | 14.4 | 0.868 | 0.717 |

11. The process of claim 1, wherein the acid-catalyst is sulfuric acid.

12. The process of claim 1, wherein the water in the first and second steps is maintained greater than or equal to 0.8 weight percent to 4 weight percent.

13. A process for producing a phenol product, the process comprising:
- a first step comprising reacting in a first reactor a feed stream comprising cumene hydroperoxide and water with an acid catalyst to produce an effluent comprising the phenol product, acetone, and dicumyl peroxide; and
- a second step comprising passing the effluent into a second reactor and decomposing the dicumyl peroxide, wherein during said process a ratio of phenol to acetone is maintained at a molar ratio of greater than 1:1, wherein the phenol product comprises less than or equal to 40 parts per million hydroxyacetone, and wherein the process is continuous.

14. The process of claim 13, wherein the ratio of phenol to acetone is maintained at a molar ratio of greater than 1.2:1.

15. The process of claim 13 wherein the first step is maintained at a temperature of 45° C. to 75° C.

16. The process of claim 13, wherein the feed stream in the first step has a residence time of 30 seconds to 4 minutes.

17. The process of claim 13, wherein the feed stream in the first step is passed at a weighted hourly space velocity of 40 to 80.

18. The process of claim 13, wherein the second step is maintained at a temperature of 100° C. to 160° C.

19. The process of claim 13, wherein the effluent has a residence time of 5 minutes to 60 minutes in the second step.

20. The process of claim 13, wherein the effluent is passed at a weighted hourly space velocity of 8 to 20 in the second step.

21. The process of claim 13, wherein the acid-catalyst is selected from the group consisting of mineral acids, organic acids, acidic clays, and acidic ion exchange resins.

22. The process of claim 13, wherein the acid-catalyst is sulfuric acid.

23. The process of claim 13, wherein the water in the first and the second steps is maintained in an amount greater than 0 and less than or equal to 5 weight percent based on the total weight of the feed stream or the effluent.

* * * * *